(12) United States Patent
Mori et al.

(10) Patent No.: US 12,432,317 B2
(45) Date of Patent: Sep. 30, 2025

(54) DIAGNOSTIC IMAGING SUPPORT DEVICE, DIAGNOSTIC IMAGING SUPPORT SYSTEM, AND DIAGNOSTIC IMAGING SUPPORT METHOD

(71) Applicants: NATIONAL UNIVERSITY CORPORATION TOKAI NATIONAL HIGHER EDUCATION AND RESEARCH SYSTEM, Nagoya (JP); UNIVERSITY OF TSUKUBA, Tsukuba (JP)

(72) Inventors: Kensaku Mori, Nagoya (JP); Masahiro Oda, Nagoya (JP); Tetsuro Oshika, Tsukuba (JP); Yuta Ueno, Tsukuba (JP); Takefumi Yamaguchi, Chiba (JP); Hideki Fukuoka, Kyoto (JP)

(73) Assignees: NATIONAL UNIVERSITY CORPORATION TOKAI NATIONAL HIGHER EDUCATION AND RESEARCH SYSTEM, Nagoya (JP); UNIVERSITY OF TSUKUBA, Tsukuba (JP)

( * ) Notice: Subject to any disclaimer, the term of this patent is extended or adjusted under 35 U.S.C. 154(b) by 565 days.

(21) Appl. No.: 17/799,290

(22) PCT Filed: Feb. 12, 2021

(86) PCT No.: PCT/JP2021/005377
§ 371 (c)(1),
(2) Date: Aug. 12, 2022

(87) PCT Pub. No.: WO2021/162118
PCT Pub. Date: Aug. 19, 2021

(65) Prior Publication Data
US 2023/0094530 A1 Mar. 30, 2023

(30) Foreign Application Priority Data
Feb. 12, 2020 (JP) .................................. 2020-021925

(51) Int. Cl.
*H04N 7/173* (2011.01)
*H04N 5/85* (2006.01)

(52) U.S. Cl.
CPC ........... *H04N 7/17318* (2013.01); *H04N 5/85* (2013.01)

(58) Field of Classification Search
None
See application file for complete search history.

(56) References Cited

U.S. PATENT DOCUMENTS 11,974,808 B2 * 5/2024 Lim ..................... A61B 5/7267
2020/0066415 A1 * 2/2020 Hettig ................... G16H 50/30
(Continued)

FOREIGN PATENT DOCUMENTS

JP 2018-121886 A 8/2018
JP 2019-216848 A 12/2019
(Continued)

OTHER PUBLICATIONS

Apr. 20, 2021 International Search Report issued in International Patent Application No. PCT/JP2021/005377.
(Continued)

*Primary Examiner* — Darryl V Dottin
(74) *Attorney, Agent, or Firm* — Oliff PLC

(57) ABSTRACT

A diagnostic imaging support device includes: a learning unit that calculates a feature quantity about each of infectiousness condition and non-infectiousness condition for determining a condition in a determination image of an anterior eye through machine learning on the basis of a
(Continued)

learning image of an anterior eye and information about a condition in the learning image.

9 Claims, 11 Drawing Sheets

(56) References Cited

U.S. PATENT DOCUMENTS

2020/0069175 A1 3/2020 Kumagai et al.
2021/0244272 A1* 8/2021 Lim ................... G06N 3/047

FOREIGN PATENT DOCUMENTS

| WO | 2018/003906 A1 | 1/2018 |
| WO | 2019/073962 A1 | 4/2019 |

OTHER PUBLICATIONS

Apr. 20, 2021 Written Opinion issued in International Patent Application No. PCT/JP2021/005377.

De Fauw, Jeffrey et al., "Clinically applicable deep learning for diagnosis and referral in retinal disease", Nature Medicine, vol. 24, Sep. 2018, pp. 1342-1350 with 6 pages of supplemental information.

* cited by examiner

FIG.6

BREAKDOWN OF CLASSIFICATION RESULT
(THE NUMBER OF IMAGES)

|  |  | ESTIMATION RESULT | | | PERCENTAGE OF CORRECT ANSWERS |
|---|---|---|---|---|---|
|  |  | INFECTIOUSNESS | NON-INFECTIOUSNESS | NORMAL |  |
| CORRECT ANSWER | INFECTIOUSNESS | 88 | 11 | 1 | 88.0% |
|  | NON-INFECTIOUSNESS | 10 | 81 | 5 | 84.4% |
|  | NORMAL | 0 | 6 | 118 | 95.2% |

FIG.7

BREAKDOWN OF CLASSIFICATION RESULT
BY 2-FOLD CLASSIFICATION
(THE NUMBER OF IMAGES)

|  |  | ESTIMATION RESULT | | PERCENTAGE OF CORRECT ANSWERS |
|---|---|---|---|---|
|  |  | INFECTIOUSNESS | NON-INFECTIOUSNESS |  |
| CORRECT ANSWER | INFECTIOUSNESS | 89 | 10 | 89.9% |
|  | NON-INFECTIOUSNESS | 12 | 84 | 87.5% |

FIG.13

| | DETERMINATION VALUE ABOUT INFECTIOUSNESS | DETERMINATION VALUE ABOUT NON-INFECTIOUSNESS | DETERMINATION VALUE ABOUT NORMAL |
|---|---|---|---|
| R1 | 0.8 | 0.1 | 0.1 |
| R2 | 0.6 | 0.1 | 0.2 |
| R3 | 0.1 | 0.3 | 0.05 |

FIG.14A

CONSIDERED TO BE INFECTIOUS DISEASE

FIG.14B

CONSIDERED TO BE INFECTIOUS DISEASE   DETERMINATION VALUE 0.8

FIG.15

| CONDITION | DETERMINATION VALUE |
|---|---|
| INFECTIOUSNESS | 0.8 |
| NON-INFECTIOUSNESS | 0.3 |
| NORMAL | 0.2 |

FIG.16

| CONDITION | PROBABILITY VALUE |
|---|---|
| INFECTIOUSNESS | 61.5 % |
| NON-INFECTIOUSNESS | 23.1 % |
| NORMAL | 15.4 % |

FIG.17

| PROBABILITY OF ABNORMALITY | 84.6 % |

FIG.18

THERE IS HIGH POSSIBILITY
OF ABNORMALITY
AND CONSULTATION
IS RECOMMENDED

DIAGNOSTIC IMAGING SUPPORT DEVICE, DIAGNOSTIC IMAGING SUPPORT SYSTEM, AND DIAGNOSTIC IMAGING SUPPORT METHOD

TECHNICAL FIELD

The present invention relates to a diagnostic imaging support device, a diagnostic imaging support system, and a diagnostic imaging support method that determine a condition in a captured image through machine learning.

BACKGROUND ART

Software for diagnosing an eye disease on the basis of a captured image has been developed in recent years. A corresponding technique is described in Non-Patent Literature 1, for example. Such software allows support in diagnosis of the presence or absence of a disease or the type of a disease on the basis of a captured image of an eye of a subject.

Meanwhile, in conducting such a diagnosis using an image, an image captured by using specialized equipment such as an optical coherent tomography (OCT) or a fundus camera is used and a subject is required to go to a place where such pieces of equipment are installed.

CITATION LIST

Non-Patent Literature

Non-Patent Literature 1: Clinically applicable deep learning for diagnosis and referral in retinal disease. Jeffrey De Fauw, et al. (Deep Mind), Nature Medicine 24, 1342-1350 (2018)

SUMMARY OF INVENTION

Problem to be Solved by the Disclosure

Eye diseases are broadly classified into infectious diseases and non-infectious diseases and a subsequent treatment method largely differs according to these classifications. Thus, it is important to make determination of the disease classification. For example, applying a therapeutic medicine effective for a non-infectious disease to an infectious disease may conversely worsen a condition. The reverse is also true. However, making such determination is difficult unless the determination is made by an experienced medical specialist and existing techniques such as the above-described technique described in Non-Patent Literature 1 do not include a technique of making determination of the above-described classification.

For example, it is said that while both infectious conical infiltration and non-infectious corneal infiltration are to form white opaque lesions on transparent corneas, infectiousness and non-infectiousness are characterized in terms of the location or shape of the opacity, the number of the opacities, etc. An ophthalmologist makes a judgment experimentally on the basis of a finding of the opacity to decide a treatment method. In some cases, however, difficulty may be caused in making the judgment.

On the other hand, the present inventors have found that an emerging pattern such as that of an opacity observed on the cornea of an eyeball differs between an infectious disease and a non-infectious disease, and that making an assessment of whether the condition of an eyeball of a subject is to be classified into the emerging pattern in the case of an infectious disease and the emerging pattern in the case of a non-infectious disease makes it possible to provide support for diagnosis.

The present invention has been made to solve the above-described problem, and is intended to provide a diagnostic imaging support device, a diagnostic imaging support system, or a diagnostic imaging support method configured to determine a condition in a captured image of an anterior eye through machine learning.

Solution to Problem

To fulfill the above-described intention, the substance of a first invention of the present invention is a diagnostic imaging support device comprising: a learning unit that calculates a feature quantity about each of infectiousness condition and non-infectiousness condition for determining a condition in a determination image of anterior eye through machine learning on the basis of a learning image of an anterior eye and information about a condition in the learning image.

The substance of a second invention is a diagnostic imaging support device comprising: a determination unit that determines a condition in a determination image of an anterior eye using a feature quantity calculated through machine learning on the basis of a learning image of an anterior eye and information about a condition in the learning image, wherein the determination unit calculates a likelihood that the condition of determination image is each of infectiousness condition and non-infectiousness condition.

The substance of a third invention is a diagnostic imaging support device comprising: an image storage unit in which a learning image of an anterior eye and information about a condition in the learning image are stored; a learning unit that calculates a feature quantity for determining a condition in a determination image of an anterior eye through machine learning on the basis of the image storage unit; and a determination unit that determines a condition in the determination image of the anterior eye using the feature quantity, wherein the determination unit calculates a likelihood that the condition of determination image is each of infectiousness condition and non-infectiousness condition.

Advantageous Effect of the Invention

According to the first invention, the learning unit calculates a feature quantity about each of infectiousness condition and non-infectiousness condition for determining a condition in a determination image of anterior eye through machine learning on the basis of a learning image of an anterior eye and information about a condition in the learning image.

According to the second invention, the determination unit determines a condition in a determination image of an anterior eye using a feature quantity calculated through machine learning. The determination unit calculates a likelihood that the condition of the determination image is each of infectiousness condition and non-infectiousness condition. By doing so, the likelihood is contained in determination result to acquire reliability of condition provided in the determination result.

According to the third invention, in relation to a determination image of an anterior eye, a condition in this image can be determined through machine learning on the basis of the image storage unit in which a learning image of an anterior eye and information about a condition in the learning image are stored in advance. The determination unit calculates a likelihood that the condition of the determination image is each of infectiousness condition and non-infectiousness condition. By doing so, the likelihood is contained in determination result to acquire reliability of condition provided in the determination result.

Preferably, according to a fourth invention, in the second or third invention, the determination unit further calculates a likelihood that the condition of the determination image is of normal condition. By doing so, the likelihood is contained in determination result to acquire reliability of a condition provided in the determination result.

Preferably, according to a fifth invention, in any one of the second to fourth inventions, the determination unit determines whether the condition of the determination image is of any of conditions including an infectious disease, a non-infectious disease, and normal. This makes it possible to determine whether an anterior eye in a captured image is in any of conditions including an infectious disease, a non-infectious disease, and normal.

Preferably, according to a sixth invention, in any one of the second to fifth inventions, the determination unit calculates an evaluation value for evaluation of the determination image on the basis of the feature quantity in the determination image calculated about each of the conditions of infectious, non-infectious, and normal. This allows calculation of the evaluation value for evaluation of the determination image differing from the feature quantity on the basis of the feature quantity. For example, one evaluation value can be calculated on the basis of a plurality of feature quantities to facilitate evaluation.

Preferably, according to a seventh invention, in any one of the second to fifth inventions, a likelihood that the condition of the determination image is of each of conditions including infectiousness, non-infectiousness, and normal, or an evaluation value is calculated and output. By doing so, machine learning is performed on the basis of the learning image of the anterior eye and the information about the condition in the learning image. Furthermore, using result of the machine learning, it is possible to acquire a likelihood that a condition is each of infectiousness, non-infectiousness, and normal or information about the evaluation value. Acquiring the highest likelihood or information about the condition of the evaluation value not only makes it possible to provide information for selection of a treatment method suited for the condition but also makes it possible to acquire information about a condition of a low likelihood or a low evaluation value. This is useful as information necessary for making judgment as to avoidance of an unfavorable therapeutic medicine is provided if applying this medicine to a condition of a low likelihood or a low evaluation value will cause side effect, etc.

Preferably, according to an eighth invention, in the sixth invention, the determination unit calculates the evaluation value by applying the feature quantity in the determination image calculated about each of the conditions of infectiousness, non-infectiousness, and normal to a Softmax function. This allows the evaluation value to be calculated as a value from 0 to 1 to facilitate evaluation using the evaluation value.

Preferably, according to a ninth invention, in the sixth or eighth invention, the determination unit selects at least one from a plurality of sentences stored in advance in response to the evaluation value and outputs the selected sentence. By doing so, the sentence responsive to the evaluation value is output to allow evaluation to be acquired intuitively.

Preferably, according to a tenth invention, in any one of the second to ninth inventions, the determination unit estimates a disease name. This allows acquisition of information about the estimated disease name in addition to information about the condition of the anterior eye.

Preferably, according to an eleventh invention, in any one of the third to tenth inventions, the learning unit performs the machine learning again on the basis of a condition confirmed in determination made in the past by the determination unit. This allows update of the machine learning on the basis of the determination already made by the determination unit and the validity of the determination.

Preferably, according to a twelfth invention, in any one of the second to eleventh inventions, an image cutout unit is provided that detects the position of a determination main part in the determination image and cuts out an image in such a manner as to cover the position of the determination main part, and the determination unit determines the condition of the anterior eye from a cutout image resulting from the cutout by the image cutout unit. By doing so, it is only required to capture an image in such a manner as to cover the anterior eye during the imaging, thereby increasing the flexibility of images to be handled.

Preferably, according to a thirteenth invention, in any one of the second to twelfth inventions, a camera for capturing an image covering an anterior eye of a subject is provided. By doing so, an image covering an anterior eye is captured using the camera of the diagnostic imaging support device. This allows an image to be captured and allows determination about this image to be made by the same diagnostic imaging support device. Also preferably, the camera is used for capturing a visible image under visible light. By doing so, general-purpose camera units mounted on various types of devices become available.

Preferably, a fourteenth invention is a diagnostic imaging support system having a configuration comprising: the diagnostic imaging support device according to any one of the second to twelfth inventions; and a terminal device configured to communicate information with the diagnostic imaging support device, wherein the terminal device includes: a camera for capturing an image covering an anterior eye of a subject; and a transmission unit that transmits the image captured by the camera to the diagnostic imaging support device, and the diagnostic imaging support device determines the condition of the anterior eye of the subject using the image transmitted from the terminal device. By doing so, as long as the terminal device with the camera and the diagnostic imaging support device are configured in a manner allowing communication of information therebetween, the terminal device and the diagnostic imaging support device are allowed to be located at separate positions. In other words, it is possible to provide diagnosis support for an image captured at a separate position. Also preferably, the camera is used for capturing a visible image under visible light. By doing so, general-purpose camera units mounted on various types of devices become available.

Preferably, a fifteenth invention is a diagnostic imaging support method comprising: a learning step of performing machine learning on the basis of a learning image of an anterior eye and information about a condition in the learning image; and a determination step of determining a condition in a determination image using learning result obtained in the learning step, wherein the determination step each calculates a likelihood that the determination image is of infectiousness and non-infectiousness. By doing so, machine learning is performed on the basis of the learning image of the anterior eye and the information about the condition in the learning image. Furthermore, using result of the machine learning, it is possible to determine a condition in the determination image. By doing so, the likelihood is contained in determination result to acquire reliability of a condition provided in the determination result.

Preferably, a sixteenth invention is a diagnostic imaging support method comprising: a learning step of performing machine learning on the basis of a learning image of an anterior eye and information about a condition in the learning image; a likelihood calculation step of calculating a likelihood that a condition in a determination image is each of conditions including infectiousness and non-infectiousness using learning result obtained in the learning step; and an output step of outputting an evaluation value about the determination image each of infectiousness and non-infectiousness calculated on the basis of the likelihood or outputting the likelihood. By doing so, machine learning is performed on the basis of the learning image of the anterior eye and the information about the condition in the learning image. Furthermore, using result of the machine learning, it is possible to acquire information about an evaluation value or a likelihood that a condition in the determination image is any of infectiousness, non-infectiousness, and normal. As a treatment policy largely differs between infectiousness and non-infectiousness, this information may be provided to an ophthalmologist, for example, and can be used as diagnosis support information about a clinical state of an anterior eye. Grasping likelihood information about a condition of the highest likelihood not only provides information for selection of a treatment method suitable for the condition but also provides information about a condition of a low likelihood. This is useful as a information necessary for making judgment as to avoidance of an unfavorable therapeutic medicine is provided if applying this medicine to a condition of a low likelihood will cause side effect, etc.

Preferably, according to a seventeenth invention, in the diagnostic imaging support method according to the sixteenth invention, the likelihood calculation step includes a step of calculating each of likelihoods that a condition in the determination image is normal, and the output step includes a step of outputting an evaluation value for the determination image calculated on the basis of the likelihood or outputting the likelihood about a normal condition. By doing so, machine learning is performed on the basis of the learning image of the anterior eye and the information about the condition in the learning image. Furthermore, using result of the machine learning, it is possible to acquire information about a likelihood that a condition in the determination image is of normal. As a treatment policy largely differs between infectiousness and non-infectiousness, this information may be provided to an ophthalmologist, for example, and can be used as diagnosis support information about a clinical state of an anterior eye. Grasping likelihood information about a condition of the highest likelihood not only provides information for selection of a treatment method suitable for the condition but also provides information about a condition of a low likelihood. This is useful as a information necessary for making judgment as to avoidance of an unfavorable therapeutic medicine is provided if applying this medicine to a condition of a low likelihood will cause side effect, etc.

Preferably, according to an eighteenth invention, in the diagnostic imaging support method according to the sixteenth invention, the likelihood calculation step includes a step of setting a plurality of determination regions in the determination image and calculating a determination region likelihood indicating a likelihood that each of the determination regions is each in condition of an infectious and in condition of non-infectious, and the output step includes a step of outputting an evaluation value for the determination image calculated on the basis of the determination region likelihood of the determination region differing between an infections condition and a non-infectious condition or outputting the differing determination region likelihoods of the determination region, By doing so, machine learning is performed on the basis of the learning image of the anterior eye and the information about the condition in the learning image. Furthermore, using result of the machine learning, an ophthalmologist is provided with information about an evaluation value or a likelihood that the condition of the anterior eye is each of infectiousness and non-infectiousness as information unique to the determination image independent of selection of a determination region.

Preferably, according to an ninth invention, in the first invention, it is characterized that the learning unit calculates a feature quantity for determining a normal condition in a condition of the determination image of an anterior eye through machine learning on the basis of a learning image of an anterior eye and information about a condition in the learning image. By doing so, the learning unit further calculates a feature quantity for determining a normal condition in a condition of the determination image of an anterior eye through machine learning on the basis of a learning image of an anterior eye and information about a condition in the learning image.

BRIEF DESCRIPTION OF DRAWINGS

FIG. 6 shows one experimental result about the diagnostic imaging support device of the present invention;

FIG. 7 shows another experimental result about the diagnostic imaging support device of the present invention;

FIG. 13 explains an example of a calculated determination value;

FIG. 14 explains an example of output;

FIG. 15 explains an example of output;

FIG. 16 explains an example of output;
FIG. 17 explains an example of output; and
FIG. 18 explains an example of output.

DESCRIPTION OF EMBODIMENT

Figure 1:
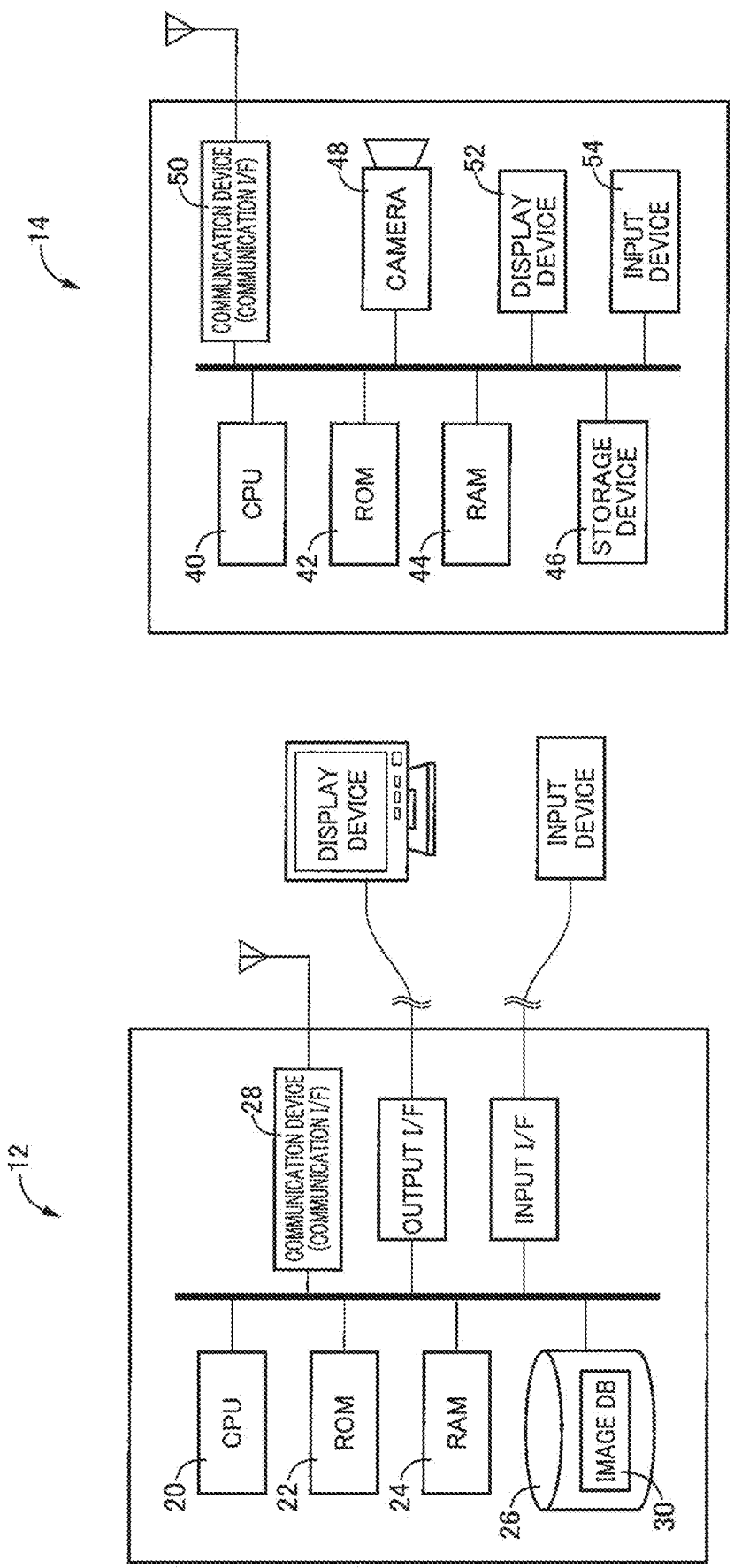
FIG. 1 explains an exemplary configuration of a diagnostic imaging support system according to an embodiment of the present invention.

Hereinafter, an embodiment of the present invention will be described in detail by referring to the drawings.

First Embodiment

FIG. 1 illustrates the configuration of a diagnostic imaging support system 10 (hereinafter called a support system 10 simply) according to an embodiment of the present invention. As shown in FIG. 1, the configuration of the support system 10 of the present embodiment includes an image processing determination device 12 and a terminal device 14. The configuration of the image processing determination device 12 includes a CPU 20 as a central processing unit, a ROM 22 as a read-only memory, a RAM 24 as a readable and writable memory, a storage device 26, and a communication device 28. The storage device 26 is preferably a publicly-known storage device (storage medium) such as a hard disk drive configured to store information. The storage device 26 may be a removable storage medium such as a compact memory card or an optical disk. The image processing determination device 12 is a so-called computer that processes and controls electronic information using the ROM 22, the RAM 24, etc. on the basis of a certain program stored in advance in the storage device 26, for example. If necessary, the image processing determination device 12 may be provided with an input device such as a keyboard or a mouse for accepting input from an operator or an output device such as a display or a printer. These input and output devices are connected through an input and output interface to the image processing determination device 12.

The communication device 28 is a so-called network interface and forms connection in a manner allowing communication of information with another device in any connection method that is either through a wire or without a wire. According to the present embodiment, the image processing determination device 12 and the terminal device 14 are connected to each other through wireless communication in a manner allowing communication of information.

The storage device 26 is provided with an image database 30. The image database 30 corresponds to an image storage unit of the present invention. The image database 30 contains a plurality of images resulting from imaging of anterior eyes as learning images and contains information as a label about the condition of the anterior eye in relation to each of these images. According to the present embodiment, the condition of the anterior eye is any one of an infectious disease, a non-infectious disease, and a normal condition. The anterior eye means a part anterior to the crystalline lens of an eyeball. According to the present embodiment, this anterior eye corresponds to an eyeball or a cornea of a subject, which is a part of the subject observable from outside. A plurality of the images are images of anterior eyes captured in advance as cases. These images are obtained by a visible camera under visible light, for example, and are comparable to what are observed from outside by a doctor in examining anterior eyes of patients. The information about the condition of the anterior eye is a result obtained by actually examining and diagnosing a subject corresponding to an image of this anterior eye by a medical specialist, for example.

As shown in FIG. 1, the terminal device 14 includes a CPU 40, a ROM 42, a RAM 44, and a communication device 50. The functions of these units are the same as those of the CPU 20, the ROM 22, the RAM 24, and the communication device 28 of the image processing determination device 12 respectively. The terminal device 14 includes a storage device 46. The storage device 46 may be a publicly-known storage medium such as a semiconductor memory configured to store information or may be a hard disk drive, for example, like the storage device 26 of the image processing determination device 12. The terminal device 14 is a so-called computer that processes and controls electronic information using the ROM 42, the RAM 44, etc. on the basis of a certain program stored in advance in the ROM 42 or the storage device 46, for example. If the volume of information to be stored in the terminal device 14 can be covered sufficiently in the RAM 44, the storage device 46 is not required.

The terminal device 14 includes a camera 48 as an imaging device, a display device 52 such as a liquid crystal panel, for example, and an input device 54 for accepting operation by an operator. For example, a transmissive touch panel superimposed on the display device 52 may be provided as the input device 54. If necessary, the terminal device 14 may be provided with an input device such as a keyboard or a mouse for accepting input from an operator or an output device such as a display or a printer. These input and output devices are connected through an input and output interface to the terminal device 14.

The storage device 46 contains a program for motion by the terminal device 14, and additionally, contains an image captured by the camera 48 or information transmitted from another device through the communication device 50.

The camera 48 is a visible light camera for imaging under visible light. The camera 48 stores a captured image as electronic data in a certain format and stores the electronic data into the above-described storage device 46, for example. The display device 52 makes a display about motion by the terminal device 14, more specifically, operation or setting for the camera 48 or displays a preview of an image to be captured. The input device 54 is to accept operation on the terminal device 14, functions as a shutter switch of the camera 48, for example, and is used for performing operation for transmitting a captured image to the image processing determination device 12.

Figure 2:
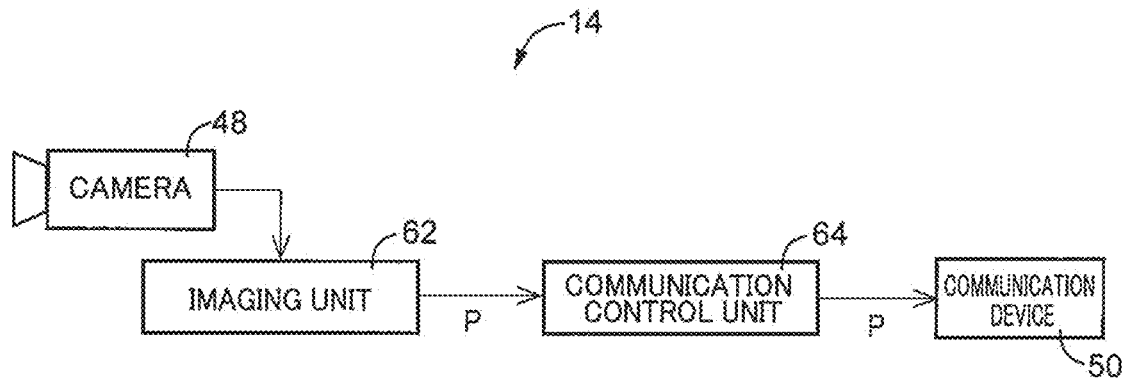
FIG. 2 is a block diagram explaining a principal part of a function of a terminal device forming the diagnostic imaging support system in FIG. 1.

FIG. 2 is a functional block diagram explaining a principal part of a control function provided to the terminal device 14. As shown in FIG. 2, the configuration of the terminal device functionally includes an imaging unit 62 and a communication control unit 64. In response to operation by an operator through the input device 54, the imaging unit 62 controls the camera 48 to capture an image covering an anterior eye of a subject (hereinafter called a subject image P). The imaging unit 62 stores the captured subject image P into the storage device 46.

The communication control unit 64 transmits the subject image P stored in the storage device 46 to the image processing determination device 12 through the communication device 50.

Figure 3:
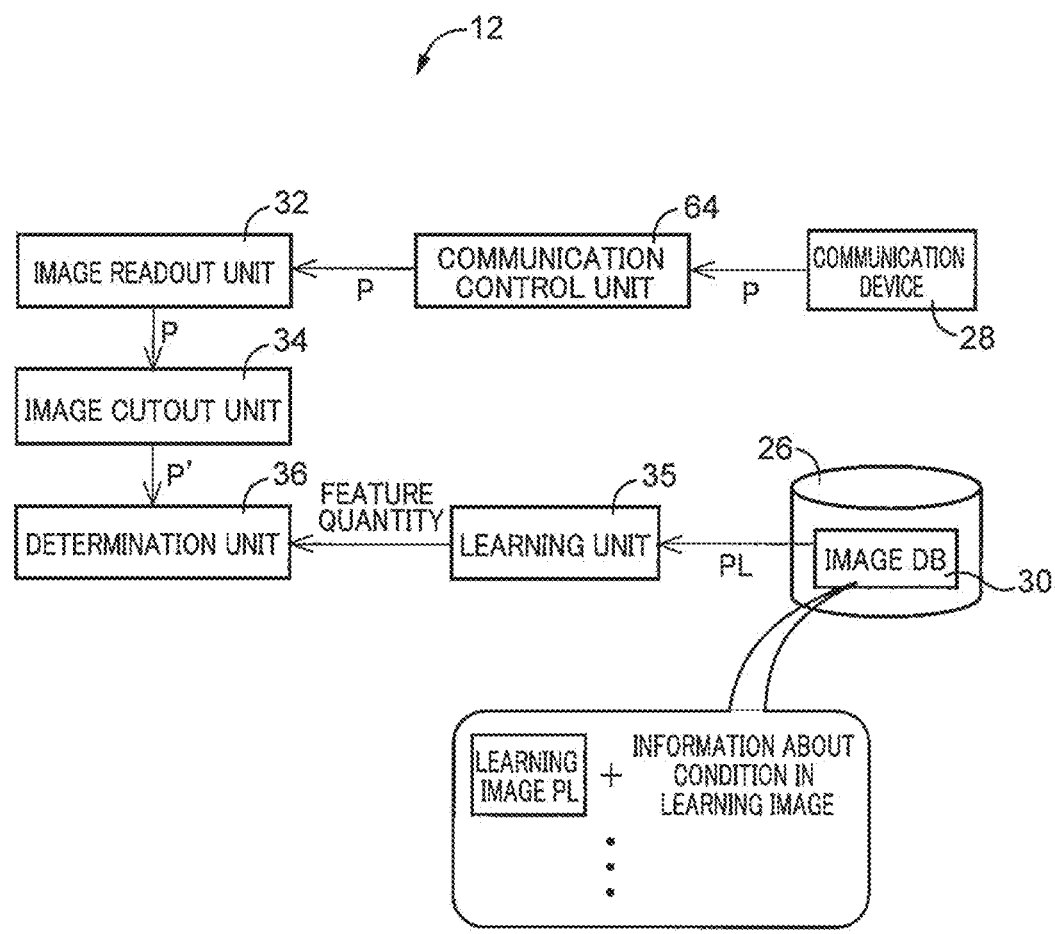
FIG. 3 is a block diagram explaining a principal part of a function of a diagnostic imaging support device forming the diagnostic imaging support system in FIG. 1.

FIG. 3 is a functional block diagram explaining a principal part of a control function provided to the image processing determination device 12. As shown in FIG. 3, the image processing determination device 12 functionally includes an image readout unit 32, an image cutout unit 34, a learning unit 35, and a determination unit 36.

Of these units, the image readout unit 32 reads out the subject image P as a target of determination by the determination unit 36 described later. For example, the subject image is an image received by a communication control unit 64 and stored in the storage device 26.

The image cutout unit 34 cuts out a certain shape such as a rectangular shape, for example, from the subject image P read out by the image readout unit 32 in such a manner that an anterior eye, more specifically, a cornea occupies a major part of the image, and stores the cutout shape as a cutout image P'. For example, the cutout may be made in such a manner that the cornea is covered entirely in the cutout image P' and the number of pixels in the cutout image P' from an end portion of the cornea to an end portion of the image becomes equal to or greater than a predetermined number. Alternatively, the cutout may be made in such a manner that an end portion of the cornea is covered at least partially in the cutout image P'. The image cutout unit 34 may cut out an image on the basis of a predetermined algorithm, for example, or may cut out an image in response to operation by an operator, more specifically, may cut out a region of a shape designated by the operator in the subject image P. By doing so, in capturing the subject image P, it becomes unnecessary to make position adjustment so as to locate the cornea at the center of the image or so as to set the cornea in an intended size in the image in the imaging. The cutout image P' corresponds to a determination image and a region including the cornea corresponds to a determination main part. If the subject image P is suitable for determination by the determination unit 36 described later, the image cutout unit 34 is not required to generate the cutout image P'. In other words, the cutout image P' as it is may be the subject image P. In other words, in such a case, the captured subject image P corresponds to the determination image.

The learning unit 35 calculates a feature quantity through machine learning to be used for determination of the cutout image P' by the determination unit 36 described later. More specifically, the learning unit 35 calculates the feature quantity as follows. First, the learning unit 35 calculates a feature quantity in advance from each learning image PL in the image database 30 indicating a feature of this image. According to the present embodiment, in response to information indicating a condition in each image of the learning images PL stored in the image database 30, specifically, in response to a condition in each image that is any one of infectiousness, non-infectiousness, and normal, a feature quantity is calculated from the corresponding learning images PL in each of the conditions. By doing so, a feature quantity is calculated about each of infectiousness, non-infectiousness, and normal. The calculated feature quantity is stored in a storage device in the device 12 such as the storage device 26, for example. As a more specific example, this calculation of a feature quantity is made by following an algorithm such as YOLOv3 suggested by Joseph Redmon et al., for example. This motion by the learning unit 35, specifically, this calculation of a feature quantity corresponds to a learning step.

The determination unit 36 determines a condition in an image of an anterior eye in the cutout image P' cut out by the image cutout unit 34 is any one of an infectious disease, a non-infectious disease, and normal. The determination unit 36 makes the determination by giving consideration to similarity between the feature quantity about each condition calculated by the learning unit 35 and the cutout image P'. As a more specific example, the determination unit 36 makes the determination by following an algorithm such as YOLOv3 suggested by Joseph Redmon et al. Specifically, the determination unit 36 randomly sets a plurality of rectangular regions having rectangular shapes as regions for determination (determination regions) differing from each other in size or position, compares each of these rectangular regions individually, with a feature quantity about each condition stored, for example, in the storage device 26, and sets a determination value (likelihood). (While the determination region is a rectangular region in the case described below, the determination region may have any shape except a rectangular shape.) Increase in this determination value means higher similarity between a teacher image about each condition and the cutout image P'. Specifically, if the cutout image P' is reliably estimated to be infectious, a calculated determination value about infectiousness is 1. If the cutout image P' is reliably estimated not to be infectious, a calculated determination value is 0. Determination values are set in the same way for non-infectiousness and normal.

As described above, a feature quantity is calculated and stored in response to each condition of an anterior eye in the learning image PL that is any one of an infectious disease, a non-infectious disease, and normal. Regarding a feature quantity used as a target in giving the highest determination value, the determination unit 36 determines a condition in a learning image corresponding to this feature quantity that is any one of an infectious disease, a non-infectious disease, and normal to be a condition in the cutout image P'. This motion by the determination unit 36, specifically, calculation of determination values and making determination through comparison between the determination values correspond to a determination step.

Figure 4:
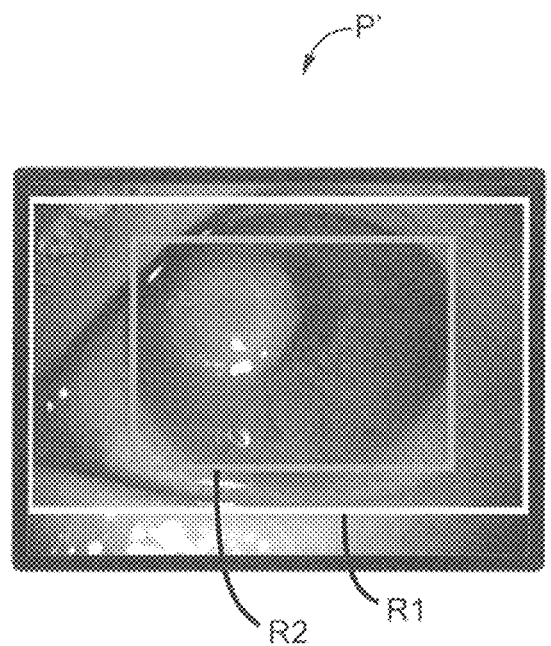
FIG. 4 explains an outline of motion by a determination unit in FIG. 3.

FIG. 4 explains an outline of the determination motion by the determination unit 36. A rectangle R1 and a rectangle R2 in FIG. 4 show two of a plurality of rectangular regions set in the cutout image P' by the determination unit 36. The determination unit 36 determines that, of feature quantities calculated by the learning unit 35, the rectangle R1 is similar to a feature quantity about a condition indicating a non-infectious disease, and that the rectangle R1 has a determination value PH, On the other hand, the determination unit 36 determines that, of the feature quantities calculated by the learning unit 35, the rectangle R2 is similar to a feature quantity about a condition indicating an infectious disease, and that the rectangle R2 has a determination value Pr2. In this case, the determination unit 36 compares the determination values Pr1 and Pr2 with each other and employs a rectangle of the highest determination value as a determination result. Specifically, if Pr1<Pr2, the rectangle R2 is employed as a determination result. Thus, a condition in the cutout image P' is determined to be an infectious disease that is a condition corresponding to the feature quantity to which the rectangle R2 is determined to be similar.

Figure 5:
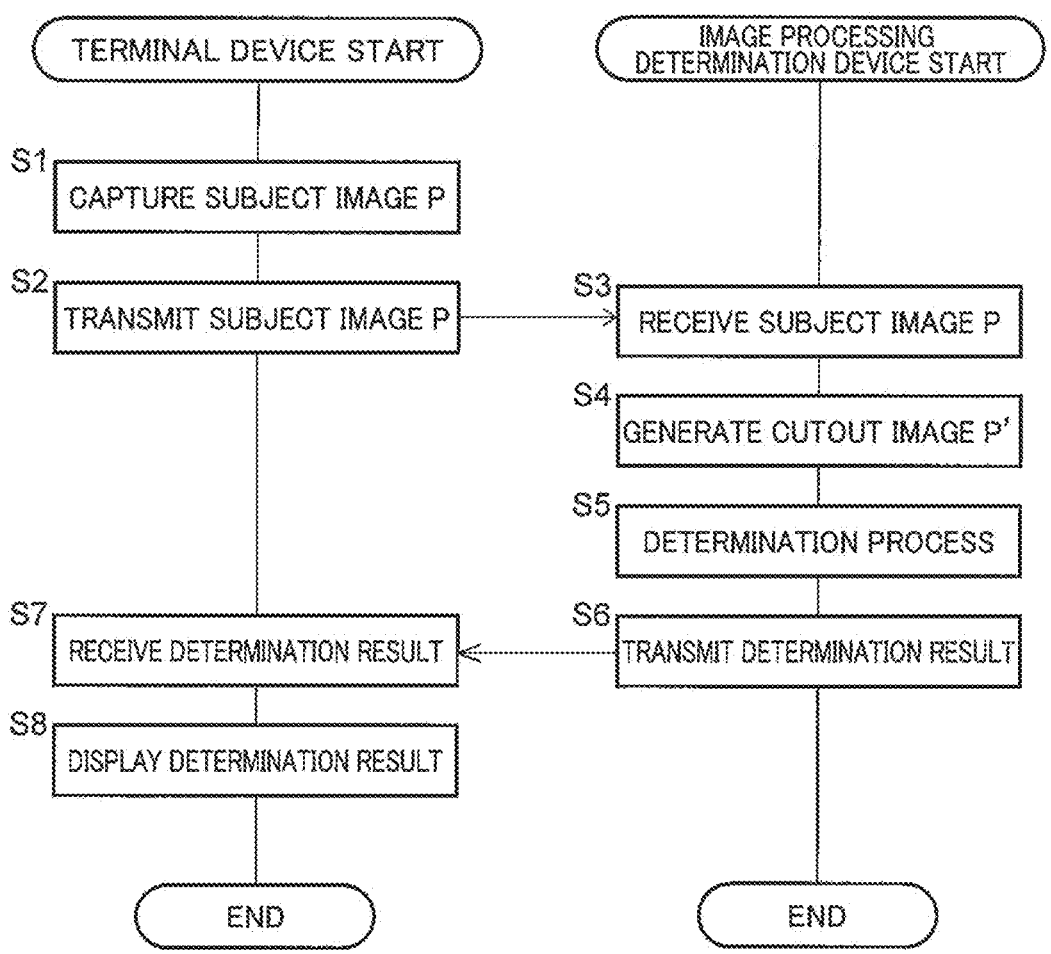
FIG. 5 is a flowchart explaining an example of control motion by the diagnostic imaging support system in FIG. 1.

FIG. 5 is a flowchart explaining an example of control motion by the diagnostic imaging support system 10 according to the present embodiment and shows motion by the terminal device 14 and motion by the image processing determination device 12 in comparison with each other. Calculation of a feature quantity by the learning unit 35 of the image processing determination device 12 is not illustrated as this calculation is made before execution of this flowchart. In other words, this flowchart is executed while a feature quantity is obtained.

First, in step (the term "step" will be omitted below) S1 corresponding to the imaging unit 62 of the terminal device 14, on the basis of operation by an operator, an image of an anterior eye of a subject is captured as the subject image P. At this time, the operator may be the same as or different from the subject. As described above, the subject image P is not required to be an image covering only the anterior part but may be an image of an entire face or an image further covering a part of a face as long as the image covers the anterior eye.

In S2 corresponding to the communication control unit 64 of the terminal device 14, the subject image P captured in S1 is transmitted from the terminal device 14 to the image processing determination device 12. This transmission is made in a manner allowing communication of information without a wire such as a so-called wireless LAN or a cell phone line.

In S3 corresponding to the communication control unit 64 of the image processing determination device 12, the subject image P transmitted in S2 is received and stored into the storage device 26 or the RAM 24, for example.

Next, in S4 corresponding to the image cutout unit 34, the cutout image P' is cut out as an image specialized for the anterior eye from the subject image P received in S3. This cutout image P' is obtained by making a cutout into a predetermined certain shape such as a rectangle, for example, from the subject image P in such a manner that the cutout covers the anterior eye, specifically, a cornea and a part other than the cornea is reduced as much as possible.

In S5 corresponding to the determination unit 36, the condition of the anterior eye in the cutout image P' cut out in S4 is determined through machine learning. Specifically, a plurality of rectangular regions R is set in the cutout image P', each of these rectangular regions R is compared with a feature quantity about a corresponding condition, and similarity is calculated as a determination value. A condition corresponding to a feature quantity of the highest determination value is determined to be a condition in the cutout image P'.

In S6 corresponding to the communication control unit 64, determination result obtained in S5 is transmitted to the terminal device 14.

In S7 corresponding to the communication control unit 64 of the terminal device 14, the determination result transmitted in S6 is received. In S8, the determination result received in S7 is displayed on the display device 52 of the terminal device 14. By doing so, the determination result is displayed on the display device 52 provided to the terminal device 14 by which the subject image P was captured. This allows the subject to see the determination result even if the terminal device 14 at the same place as the subject is separated from the image processing determination device 12.

Experimental Example 1

To verify the effectiveness of the diagnostic imaging support device of the present invention, the present inventors prepared 320 anterior eye images and conducted evaluation experiment by 5-fold cross validation. Specifically, the 320 anterior eye images are divided into five groups. With one of these groups set as the subject images P and the other four groups as the learning images PL, the subject images P were subjected to determination sequentially in such a manner that all these five groups are used as the subject images P by following the way described in the above-described embodiment. Of the 320 anterior eye images, 100 images indicate infectious diseases, 96 images indicate non-infectious diseases, and 124 images indicate normal conditions.

FIG. 6 shows determination result. As shown in FIG. 6, of the 100 images indicating infectious diseases, the diagnostic imaging support device of the present invention, namely, the determination unit 36 of the present embodiment determined that 88 of these images are of infectious diseases to result in a percentage of correct answers of 88%. Of the 96 images indicating non-infectious diseases, the diagnostic imaging support device of the present invention determined that 81 of these images are of non-infectious diseases to result in a percentage of correct answers of 84.4%. Of the 124 images indicating normal conditions, the diagnostic imaging support device of the present invention determined that 118 of these images are of normal conditions to result in a percentage of correct answers of 95.2%. In total, correct determinations were made for 287 out of 320 to result in a percentage of correct answers of 89.7%. In this way, the diagnostic imaging support device of the present invention was found to be configured to output determination result with high accuracy.

Experimental Example 2

Next, 195 anterior eye images were prepared and evaluation experiment by 5-fold cross validation was conducted like in the experimental example 1 described above. The 195 anterior eye images of the present experimental example include 99 images indicating infectious diseases and 96 images indicating non-infectious diseases without images indicating normal conditions. Thus, the determination unit 36 was to made determination (2-fold) between the two classifications.

FIG. 7 shows determination result. As shown in FIG. 7, of the 99 images indicating infectious diseases, the diagnostic imaging support device of the present invention determined that 89 of these images are of infectious diseases to result in a percentage of correct answers of 89.9%. Of the 96 images indicating non-infectious diseases, the diagnostic imaging support device of the present invention determined that 84 of these images are of non-infectious diseases to result in a percentage of correct answers of 87.5%. In total, correct determinations were made for 173 out of 196 to result in a percentage of correct answers of 88.3%.

Meanwhile, the inventors of the present application made a comparative example in cooperation with doctors. During implementation of the comparative example, 196 anterior eye images were presented to 27 ophthalmologists (hereinafter called "doctors") and the doctors made classification between two indicating whether these images are of infectious diseases or whether these images are of non-infectious diseases. Of the 196 anterior eye images according to the present comparative example, 100 images indicate infectious diseases and 96 indicate non-infectious diseases. The 27 doctors include specialists and non-specialists of cornea. According to the present comparative example, the doctors produced a percentage of correct answers of 86.7% for anterior eye images of infectious diseases and 74.9% for anterior eye images of non-infectious diseases. A percentage of correct answers was 80.9% for the 196 anterior eye images in total. In further comparison to the determination result obtained by the doctors, the determination result obtained by the diagnostic imaging support device of the present invention was found to be comparable to that by the doctors at least in its percentage of correct answers.

According to the diagnostic imaging support system 10 of the present embodiment, on the basis of the learning image PL of an anterior eye and information about a condition in the learning image PL, the learning unit 35 calculates a feature quantity for determining a condition in a captured image of an anterior eye through machine learning.

According to the diagnostic imaging support system 10 of the present embodiment, the determination unit 36 determines a condition in a determination image of the anterior eye using the feature quantity calculated through machine learning.

The diagnostic imaging support system 10 of the present embodiment includes the image processing determination device 12 including: the image database 30 in which the learning image PL of the anterior eye and the information about the condition in the learning image PL are stored; and the determination unit 36 that determines a condition in the subject image P through machine learning on the basis of the image database 30. This allows the subject image P as a captured image of an anterior eye of a subject to be subjected to determination of a condition in the subject image P through machine learning.

According to the diagnostic imaging support system 10 of the present embodiment, the determination unit 36 determines whether the captured subject image P is of any of conditions including an infectious disease, a non-infectious disease, and normal.

The diagnostic imaging support system 10 of the present embodiment includes the image cutout unit 34 that detects the position of a cornea from the subject image P and cuts out an image in such a manner as to cover the position of the cornea. The determination unit 36 determines the condition of the anterior eye from the cutout image P' cut out by the image cutout unit 34. Thus, it is only required to capture an image in such a manner as to cover the anterior eye during the imaging, thereby increasing the flexibility of images to be handled.

The configuration of the diagnostic imaging support system 10 of the present embodiment includes the image processing determination device 12 and the terminal device 14 configured to communicate information with the image processing determination device 12. The terminal device 14 has a configuration including the camera 48 for capturing an image covering an anterior eye of a subject, and the communication device 50 that transmits the subject image P captured by the camera 48 to the image processing determination device 12. The image processing determination device 12 determines the condition of the anterior eye of the subject using the subject image P transmitted from the terminal device 14. Thus, as long as the terminal device 14 with the camera 48 and the image processing determination device 12 are configured in a manner allowing communication of information therebetween, the terminal device 14 and the image processing determination device 12 are allowed to be located at physically separate positions. In other words, it is possible to provide diagnosis support for an image captured at a separate position.

According to the diagnostic imaging support system 10 of the present embodiment, the camera 48 is used for capturing a visible image under visible light. This allows use of general-purpose camera units mounted on various types of devices such as smartphones, cell phones with cameras, tablet PCs, or digital cameras with communication functions, for example.

Next, another embodiment of the present invention will be described. In the following description, a member common between the embodiments will be given the same sign and description of this member will be omitted.

Second Embodiment

Figure 8:
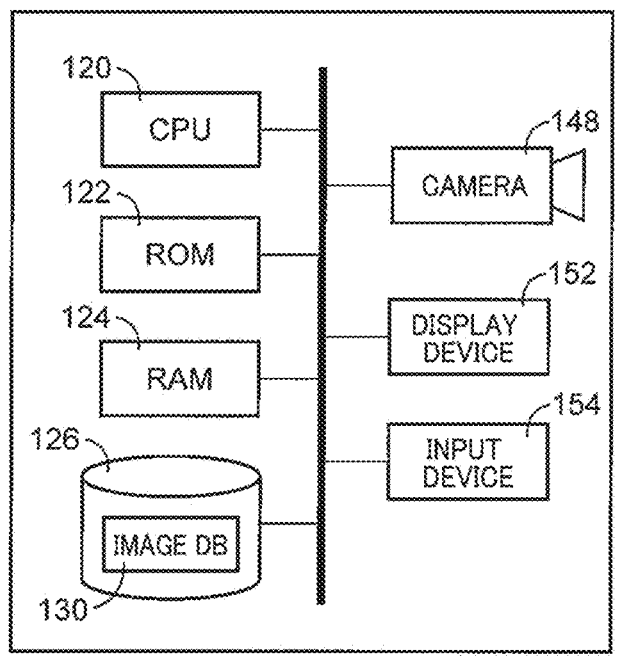
FIG. 8 shows an exemplary configuration of a diagnostic imaging support device according to another embodiment of the present invention and corresponds to FIG. 1.

FIG. 8 explains the configuration of a diagnostic imaging support device 110 according to another embodiment of the present invention. According to the above-described embodiment, the diagnostic imaging support system 10 is configured using the image processing determination device 12 and the terminal device 14. According to the present embodiment, the diagnostic imaging support device 110 alone achieves a function comparable to that of the diagnostic imaging support system 10.

As shown in FIG. 8, the configuration of the diagnostic imaging support device 110 includes a CPU 120, a ROM 122, a RAM 124, a storage device 126, a camera 148, a display device 152 as an output device, and a touch panel 154 as an input device. Preferably, hardware equipped with the display 152 with the built-in camera 148 or touch panel 154 such as a tablet PC, a smartphone, or a PDA is usable as the diagnostic imaging support device 110. In this case, an advantage is produced in terms of portability.

The CPU 120, the ROM 122, the RAM 124, the storage device 126, the camera. 148, the display device 152, and the touch panel 154 will not be described as functions thereof are the same as those of the CPU 20 or 40, the ROM 22 or 42, the RAM 24 or 44, the storage device 26 or 46, the camera 48, the display device 52, and the input device 54 of the above-described embodiment respectively.

Figure 9:
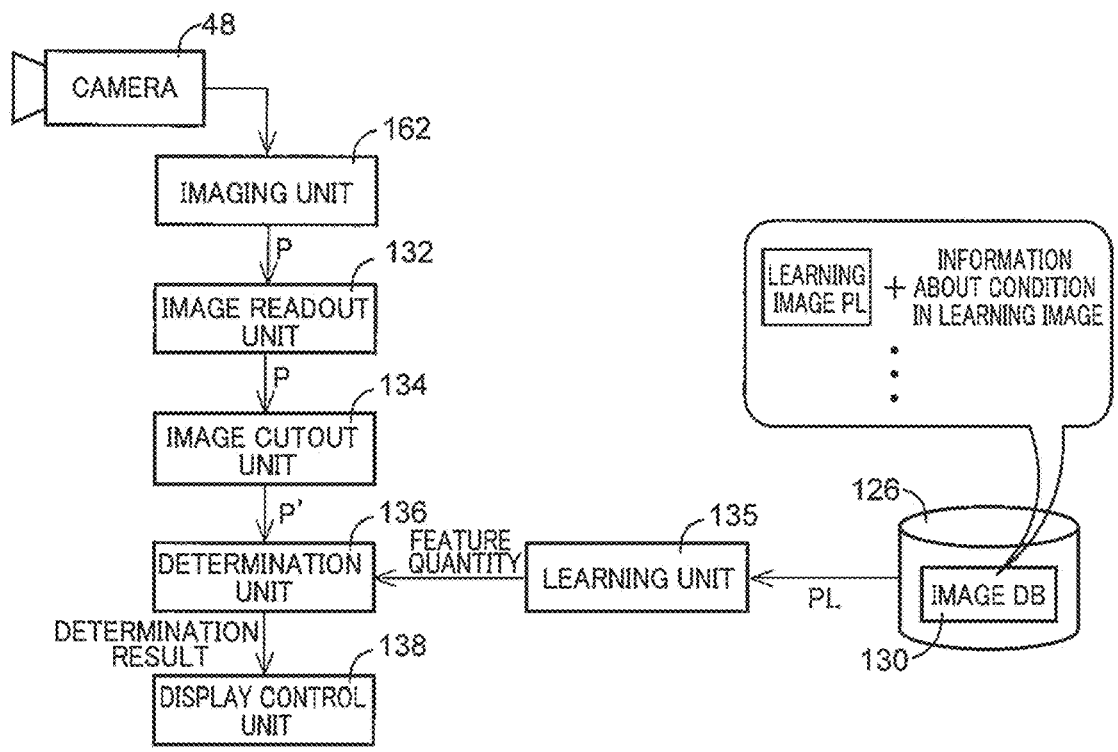
FIG. 9 is a block diagram explaining a principal part of a function of the diagnostic imaging support device in FIG. 8 and corresponding to FIGS. 2 and 3.

FIG. 9 is a functional block diagram explaining a principal part of a control function provided to the diagnostic imaging support device 110 in FIG. 1. As shown in FIG. 9, the diagnostic imaging support device 110 functionally includes an imaging unit 162, an image readout unit 132, an image cutout unit 134, a learning unit 135, a determination unit 136, and a display control unit 138.

The imaging unit 162 corresponds to the imaging unit 62 according to the above-described embodiment. In response to operation by an operator through the input device 154, the imaging unit 162 controls the camera 148 to capture an image covering an anterior eye of a subject (hereinafter called a subject image P). The imaging unit 162 stores the captured subject image P into the storage device 126 or the RAM 124, for example. At this time, by displaying a preview screen of the camera 148 on the display device 152 during the imaging, for example, a person capturing the image is given increased convenience.

The image readout unit 132 corresponds to the image readout unit 32 according to the above-described embodiment and reads out the subject image P stored in the RAM 124 or the storage device 126, for example. For example, the subject image P is an image captured by the imaging unit 162 and stored in the storage device 126 or the like.

The image cutout unit 134 corresponds to the image cutout unit 34 according to the above-described embodiment and makes similar motion. Specifically, the image cutout unit 134 cuts out a certain shape such as a rectangular shape, for example, from the subject image P read out by the image readout unit 132 in such a manner that an anterior eye, more specifically, a cornea occupies a major part of the image, and stores the cutout shape as the cutout image P'.

The learning unit 135 corresponds to the learning unit 35 according to the above-described embodiment and makes similar motion. Specifically, the learning unit 135 calculates feature quantities from the learning images PL stored in the image database 130 about respective conditions of these learning images PL, specifically, about each of an infectious disease, a non-infectious disease, and normal.

The determination unit 136 corresponds to the determination unit 36 according to the above-described embodiment and makes similar motion. Specifically, on the basis of the feature quantity about each condition calculated by the learning unit 135, the determination unit 136 determines a condition in the image of the anterior eye in the cutout image P' cut out by the image cutout unit 134 that is any one of an infectious disease, a non-infectious disease, and normal.

The display control unit 138 displays result of the determination made by the determination unit 136 on the display device 152 of the diagnostic imaging support device 110. In response to the determination result obtained by the determination unit 136, this display may be made by giving each of an indication that the subject image P is likely to be of an infectious disease, likely to be of a non-infectious disease, and likely to be of a normal condition. If the determination unit 136 determines that the subject image P is of an infectious disease or of a non-infectious disease, a message urging a subject to consult an ophthalmologist may be displayed.

Figure 10:
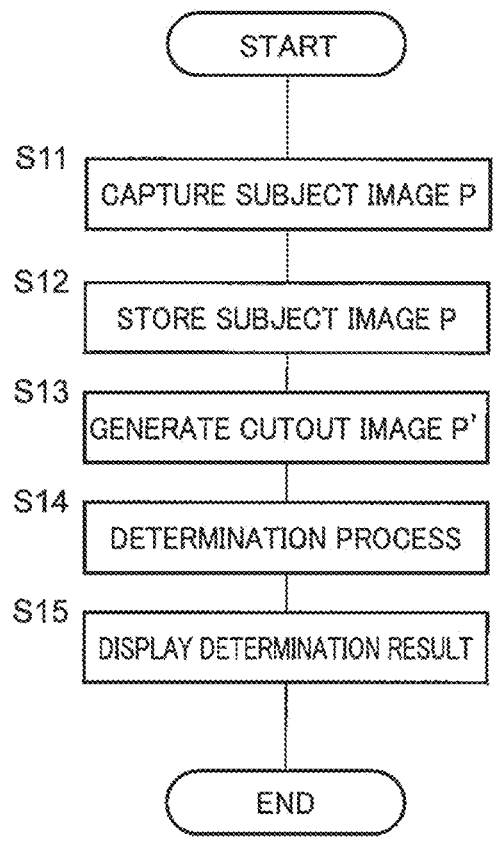
FIG. 10 is a flowchart explaining an example of control motion by the diagnostic imaging support device in FIG. 8 and corresponding to FIG. 5.

FIG. 10 is a flowchart explaining an example of control motion by the diagnostic imaging support device 110 according to the present embodiment and corresponding to FIG. 5 of the above-described embodiment.

First, in fill corresponding to the imaging unit 162, on the basis of operation by an operator, an image of an anterior eye of a subject is captured as the subject image P. In S12, this image is stored in the RAM 124 or the storage device 126, for example. At this time, the operator may be the same as or different from the subject. As described above, the subject image P is not required to be an image covering only the anterior part but may be an image of an entire face or an image further covering a part of a face as long as the image covers the anterior eye.

Next, in S13 corresponding to the image cutout unit 134, the cutout image P' is cut out as an image specialized for the anterior eye from the subject image P stored in S12. This cutout image P' is obtained by making a cutout into a predetermined certain shape such as a rectangle, for example, from the subject image P in such a manner that the cutout covers the anterior eye, specifically, a cornea and a part other than the cornea is reduced.

In S14 corresponding to the determination unit 136, the condition of the anterior eye in the cutout image P' cut out in S13 is determined through machine learning. Specifically, a plurality of rectangular regions R is set in the cutout image P', each of these rectangular regions R is compared with each of a plurality of learning images PL stored in the image database 130, and similarity is calculated as a determination value. A condition in the learning image PL of the highest determination value is determined to be a condition in the cutout image P'.

In S15, information about the determination result about the subject image P obtained in S14 is displayed on the display device 152.

The diagnostic imaging support device 110 of the present embodiment achieves effect comparable to the effect achieved by the above-described embodiment. Furthermore, the diagnostic imaging support device 110 includes the camera 148 for capturing the subject image P covering an anterior eye of a subject and the subject image P is captured using the camera 148. This allows an image to be captured and allows determination about this image to be made by the same diagnostic imaging support device 110 without requiring a network, etc. In particular, if the diagnostic imaging support device 110 is implemented using a tablet PC or a smartphone, for example, the diagnostic imaging support device with excellent portability may be provided.

Third Embodiment

The present embodiment relates to different motion by the learning unit 35 and the determination unit 36. According to the above-described first and second embodiments, the determination unit 36 sets a plurality of rectangular regions Ri in the cutout image P', calculates a determination value about each condition for each of these rectangular regions Ri, and a condition corresponding to the highest determination value is determined to be a condition in the cutout image P'. Like in the above-described embodiments, the learning unit 35 and the determination unit 36 of the present embodiment set a plurality of rectangular regions Ri, calculate a determination value about each condition for each of these rectangular regions Ri, and output an evaluation value or wording based on the evaluation value. Hereinafter, the motion by the learning unit 35 and the determination unit 36 according to the present embodiment will be described on the basis of a flowchart.

Figure 11:
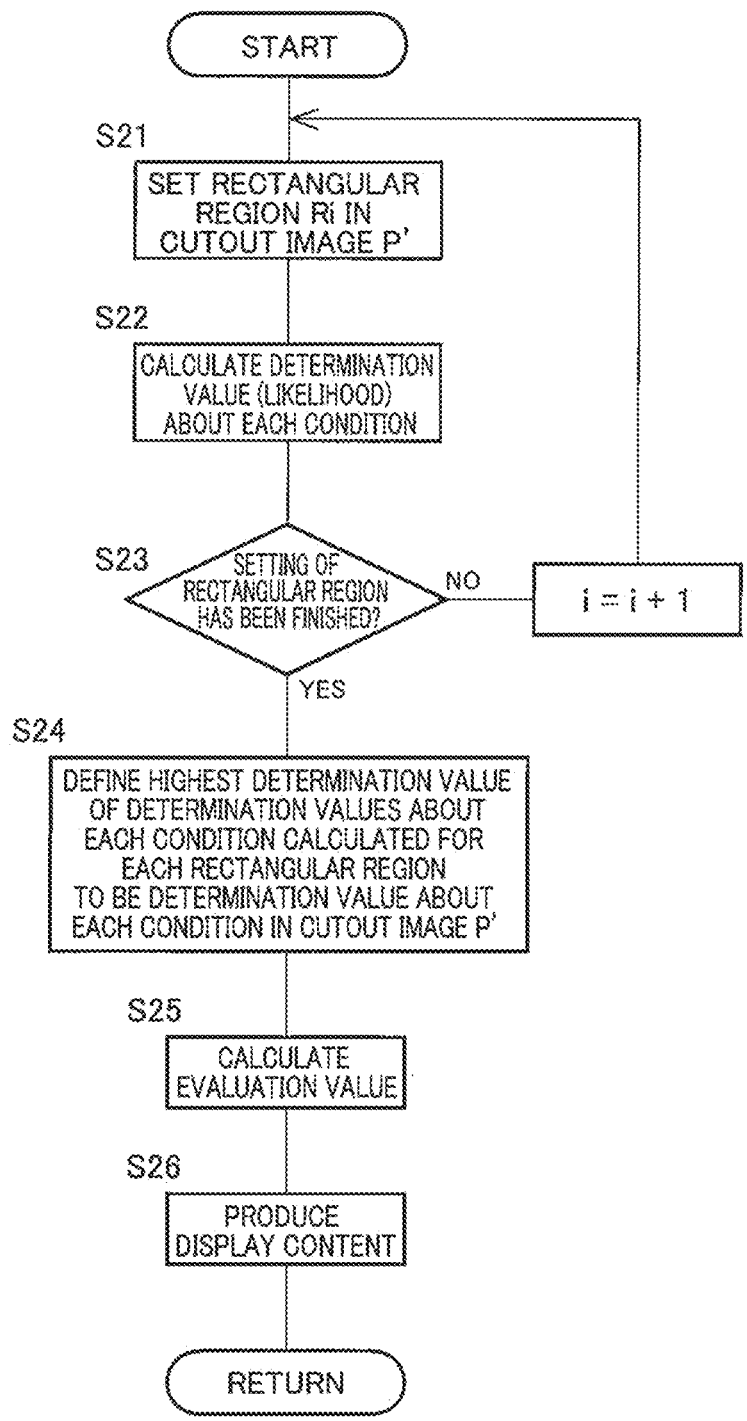
FIG. 11 is a flowchart explaining an example of motion by a learning unit and a determination unit according to another embodiment of the present invention.

FIG. 11 is a flowchart explaining an example of the motion by the learning unit 35 and the determination unit 36 according to the present embodiment. This flowchart is executed instead of the motion by the determination unit according to the above-described embodiment, more specifically, instead of S5 in FIG. 5 or S14 in FIG. 10.

In S21, one rectangular region Ri is set in the cutout image P', In S22, a determination value (likelihood) as similarity to a teacher image is calculated about each condition, specifically, about each of three conditions including infectiousness, non-infectiousness, and normal for the rectangular region Ri set in S21. The description of the motion in each of S21 and S22 will be omitted as this motion is the same as that of the above-described embodiments.

Figure 12:
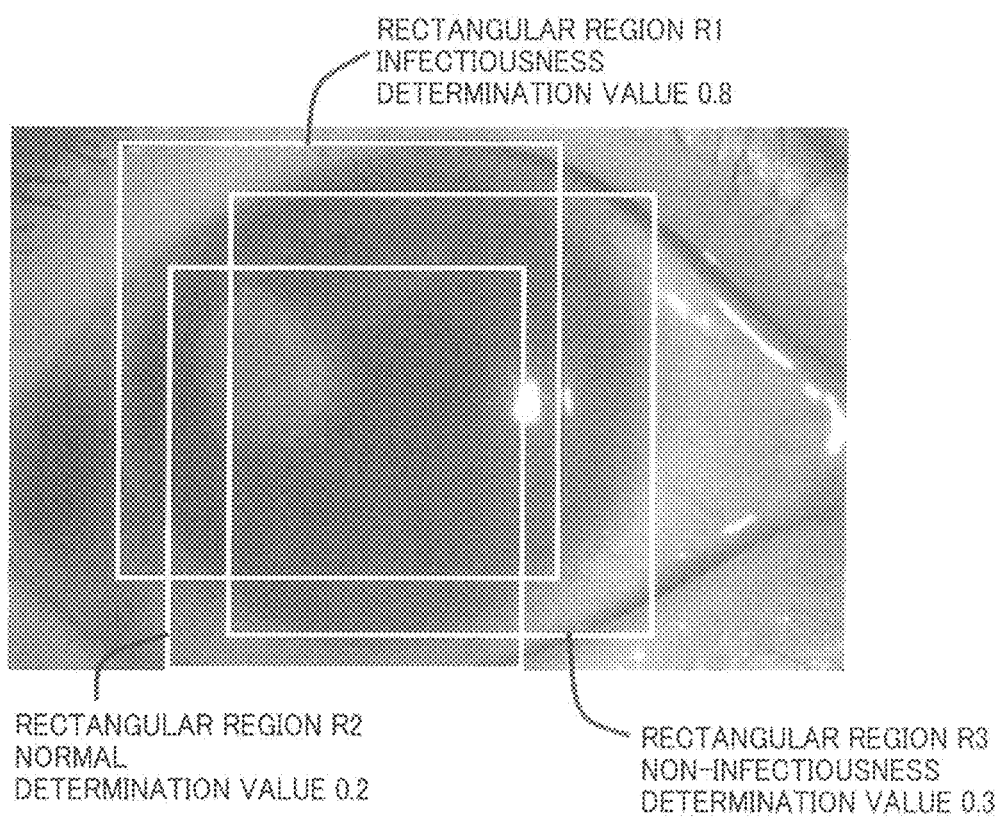
FIG. 12 explains an example of a rectangular region (determination region) and an example of a determination value corresponding to the rectangular region.

FIG. 12 explains an example of setting of the rectangular region Ri in the cutout image P'. In FIGS. 12, R1, R2, and R3 are set as three rectangular regions. The number of rectangular regions to be set is not limited to three. The learning unit 35 calculates a determination value for each of the rectangular regions R1, R2, and R3 in FIG. 12. The determination value is calculated about each of three conditions according to the present embodiment, specifically, about each of the conditions including infectiousness, non-infectiousness, and normal. As described above, by outputting or displaying a determination value (likelihood) and a corresponding determination region about each of infectiousness and non-infectiousness, an ophthalmologist is given information for diagnosing a clinical state of an anterior eye to be treated according to a treatment policy largely differing between infectiousness and non-infectiousness to determine whether this clinical state is infectiousness or non-infectiousness (or normal).

FIG. 13 explains an example of a determination value calculated about each of the three conditions, specifically, about each of infectiousness, non-infectiousness, and normal for each of the rectangular regions R1, R2, and R3. The calculated determination value is stored in a table format such as that shown in FIG. 13, for example, into a storage device not shown in the drawings.

Referring back to FIG. 11, in S23, it is judged whether a sufficient number of rectangular regions Ri have been set. A certain number is set in advance as the sufficient number in order to provide appropriate accuracy of the determination unit. This judgment is made on the basis of whether the number of the set rectangular regions Ri has reached the certain number. If the judgment in this step is made positively, calculations of determination values are judged to have been finished for the sufficient number of rectangular regions Ri. Then, S24 is performed. If the judgment in this step is made negatively, the rectangular region Ri is to be set and a determination value for the set rectangular region Ri is to be calculated continuously. Thus, executions of S21 and S22 are repeated.

In S24, a determination value corresponding to each condition is decided. As a result of repeating S21 and S23, a determination value about each condition is calculated for each of a plurality of the rectangular regions Ri. The highest value of determination values calculated for each condition is defined as a determination value about this condition. In this way, a determination value is defined about each of infectiousness, non-infectiousness, and normal for the cut-out image P'.

An outline of the motion in S24 will be described using FIG. 13. As a result of performing S21 to S23 repeatedly, a determination value is calculated about each of conditions including infectiousness, non-infectiousness, and normal for each of a plurality of the rectangular regions Ri (i=1, 2, . . . ). Then, a maximum value is searched for about each of these conditions, specifically, in each of infectiousness in the table, non-infectiousness, and columns of normal, and the searched maximum value is defined as a determination value.

Referring back to FIG. 11, in S25, an evaluation value is calculated. The evaluation value is calculated using the determination value about each condition defined in S24. As a more specific example, the evaluation value is calculated using a. Softmax function. Thus, a minimum and a maximum of the evaluation value are obtained as 0 and 1 respectively. The Softmax function is generally expressed by the following formula (1):

[Formula 1]

$$y = \frac{e^{x_j}}{\sum_{k=1}^{n} e^{x_k}} \quad (j = 1, 2, \ldots, n, \text{ herein, } n = 3) \quad (1)$$

In this formula, e is a base of a logarithm, xj is each of the defined determination value, and yj is an evaluation value to be calculated. Infectiousness, non-infectiousness, and normal indicating the conditions mentioned in the present embodiment correspond to j=1, 2, 3 respectively. In the present embodiment, as each determination value does not assume a negative value, the following formula (2) may be used. If calculation is made using formula (2), a calculated evaluation value can be a probability value (%).

[Formula 2]

$$y = \frac{x_j}{\sum_{k=1}^{n} x_k} \quad (j = 1, 2, \ldots, n, \text{ herein, } n = 3) \quad (2)$$

By doing so, it becomes possible to calculate evaluation of each of conditions including infectiousness, non-infectiousness, and normal as each evaluation value with respect to all the conditions including infectiousness, non-infectiousness, and normal.

If appropriate, a plurality of evaluation values is used in response to a method of evaluation. Each of formulas (1) and (2) described above is for an evaluation value for evaluation of each of conditions including infectiousness, non-infectiousness, and normal with respect to all the conditions including infectiousness, non-infectiousness, and normal. Meanwhile, using the following formula (3) instead of formula (1) and using the following formula (4) instead of formula (2) allows calculation as an evaluation value for evaluation of each of conditions including infectiousness and non-infectiousness with respect to the two conditions including infectiousness and non-infectiousness

[Formula 3]

$$y = \frac{e^{x_j}}{\sum_{k=1}^{2} e^{x_k}} \left( j = 1\binom{\text{infectious}-}{\text{ness}}, 2\binom{\text{non}-}{\text{infectious}-}{\text{ness}} \right) \quad (3)$$

[Formula 4]

$$y = \frac{x_j}{\sum_{k=1}^{2} x_k} \left( j = 1\binom{\text{infectious}-}{\text{ness}}, 2\binom{\text{non}-}{\text{infectious}-}{\text{ness}} \right) \quad (4)$$

Alternatively, using the following formula (5) instead of formula (1) and using the following formula (6) instead of formula (2) allows calculation as an evaluation value for evaluation of each of two conditions including infectiousness and non-infectiousness with respect to all the conditions including infectiousness, non-infectiousness, and normal, in other words, evaluation of not being normal.

[Formula 5]

$$y_{abnormal} = \frac{\sum_{k=1}^{2} e^{x_k}}{\sum_{k=1}^{n} e^{x_k}} \quad (j = 1, 2, \ldots, n, \text{ herein, } n = 3) \quad (5)$$

[Formula 6]

$$y_{abnormal} = \frac{\sum_{k=1}^{2} x_k}{\sum_{k=1}^{n} x_k} \quad (j = 1, 2, \ldots, n, \text{ herein, } n = 3) \quad (6)$$

Referring back to FIG. 11, in S26, on the basis of the determination value defined in S24 and the evaluation value calculated in S25, a display content is produced. For example, the display content to be displayed can be a condition corresponding to the highest evaluation value of evaluation values calculated about each condition. FIG. 14(a) shows an example of this display content displayed on the display device. The display content may be the highest evaluation value and a condition corresponding to this evaluation value. FIG. 14(b) shows an example of this display content. In another case, the above-described evaluation values may be displayed on the basis of each corresponding condition. FIG. 15 shows an example of display of a display content in a case where an evaluation value is calculated using formula (1). FIG. 16 shows an example of display of a display content in a case where an evaluation value is calculated using formula (2). If an evaluation value is calculated using formula (5) or formula (6), a display content may be the definition of the calculated evaluation value and a degree of the evaluation value. FIG. 17 shows an example of display of this display content.

As shown in FIGS. 12 to 16, by outputting and displaying a determination value (likelihood) or an evaluation value about each of infectiousness and non-infectiousness, an ophthalmologist is given information for diagnosing a clinical state of an anterior eye to be treated according to a treatment policy largely differing between infectiousness and non-infectiousness to determine whether this clinical state is infectiousness or non-infectiousness (or normal).

Furthermore, in FIGS. 12 to 16, a maximum value about each of the conditions including infectiousness, non-infectiousness, and normal is defined from a plurality of different determination regions and displayed as a determination value about each condition. Specifically, respective determination values about the conditions including infectiousness, non-infectiousness, and normal may be calculated from different determination regions (rectangular regions). By doing so, information about a likelihood or about an evaluation value about each of the conditions including infectiousness, non-infectiousness, and normal as the condition of an anterior eye is output as information unique to a determination image independent of selection of a rectangular region, and the output information is offered to an ophthalmologist. For example, the illustrations in FIGS. 12, 13, and 15 not only show that a high determination value of 0.8 is obtained for infectiousness but at the same time, also show that low determination values of 0.3 and 0.2 are obtained about non-infectiousness and normal respectively. Thus, the ophthalmologist is allowed to use this output information not only for choosing chemicals effective for infectious diseases but also for making a judgment of avoiding use of unfavorable chemicals if being used for non-infectiousness in terms of side effect, etc.

In S26, one or two or more sentences selected from a plurality of sentences prepared in advance may be defined as the display content. A plurality of the sentences is prepared in advance and stored in storage means not shown in the drawings, for example. Moreover, if a condition using the evaluation value is set in advance and if the evaluation value for evaluation of each of two conditions including infectiousness and non-infectiousness with respect to all the conditions including infectiousness, non-infectiousness, and normal exceeds a threshold set in advance, for example, a sentence such as "There is high possibility of abnormality and consultation is recommended." may be selected and may be employed as the display content. This threshold corresponds to the above-described condition. As an example, regarding the threshold, by assessing a relationship between a degree of an evaluation value obtained in advance by the diagnostic imaging support system 10 of the present invention and cases diagnosed as being abnormal by actual doctors, more specifically, in order to cover the cases diagnosed as being abnormal by the doctor, a value lower than evaluation values corresponding to these cases is employed as the threshold. FIG. 18 shows an example of display of this display content. Furthermore, if an evaluation value for evaluation of each of two conditions including infectiousness and non-infectiousness with respect to all the conditions including infectiousness, non-infectiousness, and normal falls under a threshold set in advance with which determination of normal can be made, a sentence such as "No problem." may be selected. In other cases, a suitable sentence is selected in response to an evaluation value. A sentence is selected not only in the case where there is one evaluation value and a threshold set in response to this evaluation value is used as a basis for the selection but also in the case where a corresponding sentence is selected for each of regions set in space of a plurality of dimensions or on a plane defined on the basis of two or more evaluation values. Alternatively, a corresponding sentence may be selected for each of regions set in space of a plurality of dimensions or on a plane defined on the basis of an evaluation value and a determination value.

According to the diagnostic imaging support system 10 and the diagnostic imaging support device 110 of the above-described embodiment, the determination unit 36 (S24, S25) calculates an evaluation value for evaluation of the determination image P' on the basis of a feature quantity in the determination image P' calculated about each of conditions including infectiousness, non-infectiousness, and normal. This allows calculation of the evaluation value for evaluation of the determination image differing from the feature quantity. In particular, one evaluation value is calculated on the basis of a plurality of three feature quantities to facilitate evaluation.

According to the diagnostic imaging support system 10 and the diagnostic imaging support device 110 of the above-described embodiment, the determination unit 36 (S24, S25) calculates the evaluation value by applying the feature quantity in the determination image calculated about each of the conditions to a Softmax function. By doing so, the evaluation value is calculated as a value from 0 to 1 to facilitate evaluation using the evaluation value.

According to the diagnostic imaging support system 10 and the diagnostic imaging support device 110 of the above-described embodiment, the determination unit 36 (S26) selects at least one from a plurality of sentences stored in advance in response to the evaluation value and outputs the selected sentence. By doing so, the sentence responsive to the evaluation value is output to allow evaluation to be acquired intuitively.

While the embodiments of the present invention have been described in detail above on the basis of the drawings, the present invention is further applicable to other configurations.

For example, the determination unit 36 or 136 according to the above-described embodiment uses YOLOv3 as a method of machine learning.

However, the method is not limited to this. Another method is applicable if this method is available for calculating a likelihood between the cutout image P' and a learning image.

Regarding each learning image PL, the image database 30 or 130 according to the above-described embodiment contains information about a condition in this image as a label, specifically, information about infectiousness, non-infectiousness, or normal. However, the information is not limited to this. For example, if the learning image PL is of infectiousness or non-infectiousness, in addition to information about whether infectiousness or non-infectiousness, a more specific disease name may be stored. In this case, instead of or in addition to making the determination according to the above-described embodiment, specifically, making the determination that the cutout image P' to be used for the determination is of infectiousness, non-infectiousness, or normal, the determination unit 36 or 136 may determine a disease name of high probability. As a more specific example, the determination unit 36 or 136 may read out information about a disease name stored in the image database 30 or 130 in relation to the learning image PL determined to have the highest similarity to the cutout image and may determine that this cutout image P' corresponds to the disease with high probability. This allows the determination unit 36 to 136 to determine a disease name of high probability on the basis of the cutout image P' instead of or in addition to making the determination that the cutout image P' is of infectiousness, non-infectiousness, or normal.

Examples of an infectious disease include bacterial keratitis, fungal keratitis, herpes virus keratitis, and amebic keratitis. Examples of a non-infectious disease include marginal corneal ulcer, catarrhal corneal ulcer, and phlyctenular keratitis.

Regarding bacterial keratitis, there are many species of bacteria such as *Staphylococcus aureus* and blue pus as causes for this keratitis. Regarding fungal keratitis, there is also a plurality of species of fungus as causes for this keratitis such as *candida* and *aspergillus*, Then, if the learning image PL is of bacterial keratitis or fungal keratitis, information about a causative microorganism causing such keratitis may also be stored in the image database 30 or 130. If the learning image PL determined to have the highest similarity to the cutout image P' by the determination unit 36 or 136 is judged to be an image of bacterial keratitis or fungal keratitis, in addition to making this judgment, the determination unit 36 or 136 may read out the information about the causative microorganism about the learning image PL determined to have the highest similarity and may determine that the cutout image P' results from this causative microorganism with high possibility. This determination is not limited to bacterial keratitis, fungal keratitis, and causative microorganisms causing bacterial keratitis, fungal keratitis but is also effective in a case where there is a correlation between a causative microorganism and a feature in an image relating to a case.

According to the above-described embodiment, the determination unit 36 or 136 determines that the cutout image P' is of infectiousness, non-infectiousness, or normal. In addition to this, the determination unit 36 or 136 may have the function of proposing a treatment method. As a more specific example, in making determination that the cutout image P' is of infectiousness, a lesion corresponding to this cutout image P' is in a condition of high possibility of cornea irritation caused by a microorganism. A germ (so-called bacterium), a fungus (so-called mold), a virus, and an ameba are representatives of the microorganism. Thus, in making determination that the cutout image P' is of infectiousness, the determination unit 36 or 136 may produce an output to propose (suggest) a treatment method such as administration of an antibiotic or an antifungal, for example, for getting rid of the microorganism. On the other hand, in making determination that the cutout image P' is of non-infectiousness, a lesion corresponding to this cutout image P' is in a condition of high possibility of cornea irritation caused by outburst of an immune mechanism of a patient himself or herself (allergic reaction such as pollen allergy, for example). In this condition, the immune mechanism causes the outburst independently on a substance not particularly harmful as a target. For example, rheumatism is one type of this condition and is known to cause "marginal corneal ulcer" at a cornea. Thus, in making determination that the cutout image P' is of non-infectiousness, an output may be produced to propose (suggest) a treatment method such as administration of an agent for suppressing immunity (immune-suppressing agent).

According to the above-described embodiment, the determination unit 36 or 136 determines that corneal infiltration as irritation in an anterior eye image is of infectiousness, non-infectiousness, or normal. However, the determination is not limited to such a disease, Specifically, diseases that are apparently similar but are to differ in appearance from each other by the causes or conditions of these diseases can be subjected to determination in the same way using the diagnostic imaging support device of the present invention. More specifically, determination can also be made if the learning image PL and the subject image P are of a case such as a corneal scar as an affected area of an irritation site or corneal degeneration caused by deposition of an abnormal substance instead of or in addition to corneal infiltration.

According to the above-described embodiment, the determination unit 36 or 136 determines that the cutout image P' is of infectiousness, non-infectiousness, or normal. However, the determination is not limited to this. For example, it can also be determined that the cutout image P' is of infectious corneal infiltration, non-infectious conical infiltration, a case other than corneal infiltration, or normal. In this case, the image database 30 or 130 contains the learning images PL of a number necessary for machine learning together with information (labels) indicating the conditions of the learning images PL stored in advance about each of infectious corneal infiltration, non-infectious corneal infiltration, a case other than corneal infiltration, and normal, and then machine learning is conducted.

According to the above-described embodiment, the image cutout unit 34 or 134 generates the cutout image P' in such a manner that a cornea occupies a major part of the cutout image P'. However, the cutout image P' is not limited to this configuration. As a more specific example, the cutout image P' may cover a cornea entirely and a part of a conjunctiva or a part of an eyelid. Preferably, the subject image P is a color image captured under visible light. This makes the cutout image P' cut out from a captured image available for determination without requiring specialized imaging equipment or imaging environment.

According to the above-described embodiment, regarding the cutout image P', the determination unit 36 or 136 defines a condition corresponding to the highest determination value as determination result about this cutout image P'. However, the definition is not limited to this configuration. For example, determination result may be a combination of the highest determination value and a condition corresponding to this determination value. This makes it possible to acquire reliability about the determination result. Alternatively, regarding at least one of the conditions including infectiousness, non-infectiousness, and normal, the highest determination value corresponding to this condition may be incorporated in determination result. By doing so, it becomes possible to understand that different judgments may be made between a plurality of conditions.

According to the above-described embodiment, the determination unit 36 or 136 calculates a feature quantity for the learning image PL stored in advance in the image database 30 or 130. However, the calculation is not limited to this configuration. For example, if the cutout image P' is subjected to determination once by the determination unit 36 or 136 and then the determined condition is confirmed by consultation or inspection, the cutout image P' used as a target of the determination and the confirmed information about the condition in this cutout image P' may be added newly to the image database 30 or 130, and a feature quantity may be calculated again. This allows the image database 30 or 130 to be updated, if appropriate. Alternatively, the image database 30 or 130 may be given information about the correctness of judgment made by the determination unit 36 or 136 about the cutout image P' as a target of the determination, and then a feature quantity may be calculated again. This achieves learning by means of so-called enforced learning.

According to the above-described embodiment, the image processing determination device 12 or the diagnostic imaging support device 110 includes: the learning unit 35 or 135 corresponding to the learning step of calculating a feature quantity in advance indicating a feature in each learning image PL in the image database 30 or 130 from each of the learning image PL; and the determination unit 36 or 136 corresponding to the determination step of calculating similarity between the cutout image P' and a learned feature quantity as a determination value (likelihood). However, the image processing determination device 12 or the diagnostic imaging support device 110 is not limited to this configuration. Specifically, if the learned feature quantity is calculated and applied in advance, what is required is only the motion of storing the applied learned feature quantity into the storage device 26 or 126, for example, and the motion corresponding to the determination step to be made using the stored learned feature quantity. Thus, a configuration including the determination unit 36 or 136 without the learning unit 35 or 135 is applicable. In this case, calculation of the learned feature quantity may be made by a learning device as a device separate from the image processing determination device 12 or the diagnostic imaging support device 110. In this case, the learning device is connected to the image processing determination device 12 or the diagnostic imaging support device 110 including the determination unit 36 or 136 in a manner allowing transmission and receipt of information including the learned feature quantity to and from the image processing determination device 12 or the diagnostic imaging support device 110. This connection may be formed through an information communication line such as a LAN or the Internet or through a connection format such as bus connection. The connection may be formed either through a wire or without a wire. By doing so, it becomes possible to fulfill a ii corresponding to the learning step and a function corresponding to the determination step using different pieces of hardware (computers) separately.

According to the above-described embodiment, the image database 30 or 130 in which the learning image PL and information about a condition in this image are stored is provided in the image processing determination device 12 or the diagnostic imaging support device 110. However, the image database 30 or 130 is not limited to this configuration. Specifically, the storage device 26 or 126 including the image database 30 or 130 may be provided as a storage device separate from the image processing determination device 12 or the diagnostic imaging support device 110. In this case, the separate storage device is connected is the image processing determination device 12 or the diagnostic imaging support device 110 including the learning unit 35 or 135 or to the above-described learning device as the separate device in a manner allowing transmission and receipt of information stored in the image database 30 or 130, etc. to and from the image processing determination device 12, the diagnostic imaging support device 110, or the learning device. This connection may be formed through an information communication line such as a LAN or the Internet or through a connection format such as bus connection. The connection may be formed either through a wire or without a wire.

In other words, if the separate storage device is provided, the image processing determination device 12 or the diagnostic imaging support device 110 is not required to include the image database 30 or 130, thereby allowing simplification of the configuration of the image processing determination device 12 or the diagnostic imaging support device 110, If the learning device as the separate device is provided, the provision of the learning unit 35 or 135 is not required. Thus, a computing unit (such as a CPU) to be mounted is only required to be suited for corresponding load and is not always required to be highly functional.

According to the above-described embodiment, the determination unit 36 or 136 makes determination each time one subject image P is captured. However, the determination is not limited to this configuration. Specifically, after readout of a plurality of subject images P, determinations may be made collectively for these subject images P.

According to the above-described first embodiment, the image processing determination device 12 and the terminal device 14 are connected to each other through a wireless LAN. However, the connection is not limited to this system but may be formed by a different wireless system. The connection may be formed with a wire using a wired LAN cable or a serial cable. While the subject image P is transmitted directly from the terminal device 14 to the image processing determination device 12, the transmission is not limited to this configuration. For example, the transmission may be made indirectly by causing the terminal device 14 to upload the subject image P to a third device on the same network and causing the image processing determination device 12 to download the uploaded subject image P from the third device, for example.

According to the above-described embodiment, a Softmax function is used for calculation of an evaluation value. However, the function is not limited to this. Specifically, a function for calculating a degree of an evaluation value from 0 to 1, in other words, for normalizing a degree of an evaluation value may be used. Another applicable function is to calculate an evaluation value to assume a degree within a certain range defined in advance not limited to a range from 0 to 1. Alternatively, a value calculated between 0 to 1 may be converted to a value in an optional range such as a range from 0 to 100, for example, and the converted value may be used as an evaluation value.

REFERENCE NUMBER DESCRIPTION

10: Diagnostic imaging support system
12: Image processing determination device
14: Terminal device
30: Image database (image storage unit)
34, 134: Image cutout unit
36, 136: Determination unit
48, 148: Camera
50: Communication device
110: Diagnostic imaging support device
P: Subject image
PL: Learning image

The invention claimed is:
1. A diagnostic imaging support device comprising:
a first processor configured to:
determine a condition in a determination image of an anterior eye using a feature quantity calculated through machine learning on a basis of a learning image of an anterior eye and information about a condition in the learning image,
calculate an evaluation value for evaluation of the determination image on a basis of the feature quantity in the determination image calculated about each of infectiousness condition, non-infectiousness condition and normal condition,
calculate a likelihood that the determination image is each of infectious condition and non-infectious condition, and
calculate the evaluation value by applying the feature quantity in the determination image calculated about each of infectiousness condition, non-infectiousness condition and normal condition to a Softmax function.
2. The diagnostic imaging support device according to claim 1, wherein the first processor determines whether the condition of the determination image is of any of conditions including infectiousness, non-infectiousness, and normal.

3. The diagnostic imaging support device according to claim 1, wherein the first processor calculates and outputs the likelihood that the condition of the determination image is of each of conditions including infectiousness, non-infectiousness, and normal, or the evaluation value for evaluation of the determination image.

4. The diagnostic imaging support device according to claim 1, wherein the first processor calculates a likelihood that the determination image is of normal condition.

5. The diagnostic imaging support device according to claim 1, wherein the first processor is further configured to select at least one from a plurality of sentences stored in advance in response to the evaluation value and outputs the selected sentence.

6. The diagnostic imaging support device according to claim 1, wherein the first processor is further configured to estimate a disease name.

7. The diagnostic imaging support device according to claim 1, wherein the first processor is further configured to:

detect a position of a determination main part in the determination image and create a cutout image by cutting out an image in such a manner as to cover the position of the determination main part, and determine the condition of the anterior eye from the cutout image.

8. The diagnostic imaging support device according to claim 1, comprising:

a camera for capturing an image covering an anterior eye of a subject.

9. A diagnostic imaging support system having a configuration comprising:

the diagnostic imaging support device according to claim 1; and a terminal device configured to communicate information with the diagnostic imaging support device, wherein the terminal device includes:

a camera for capturing an image covering an anterior eye of a subject; and a second processor, wherein the terminal device is configured to transmit the image captured by the camera to the diagnostic imaging support device, and the diagnostic imaging support device determines the condition of the anterior eye of the subject using the image transmitted from the terminal device.

* * * * *